(12) United States Patent
Giroir et al.

(10) Patent No.: US 6,509,317 B1
(45) Date of Patent: Jan. 21, 2003

(54) METHOD OF TREATING CHRONIC CARDIAC DISEASE

(75) Inventors: Brett P. Giroir, Dallas, TX (US); Patrick J. Scannon, San Francisco, CA (US)

(73) Assignees: Board of Regents, the University of Texas System, Austin, TX (US); Xoma Technology Ltd., Berkeley, CA (US)

( * ) Notice: Subject to any disclaimer, the term of this patent is extended or adjusted under 35 U.S.C. 154(b) by 0 days.

(21) Appl. No.: 09/488,979

(22) Filed: Jan. 21, 2000

Related U.S. Application Data

(60) Provisional application No. 60/116,736, filed on Jan. 22, 1999.

(51) Int. Cl.[7] .............................................. A61K 38/16
(52) U.S. Cl. ................................ 514/12; 514/2; 514/21
(58) Field of Search ................................. 514/12, 21, 2

(56) References Cited

U.S. PATENT DOCUMENTS

| | | | |
|---|---|---|---|
| 5,578,568 A | 11/1996 | Ammons et al. | 514/12 |
| 5,643,875 A | 7/1997 | Friedmann et al. | 514/12 |
| 5,646,114 A * | 7/1997 | Lambert, Jr. | 514/12 |

FOREIGN PATENT DOCUMENTS

| | | |
|---|---|---|
| WO | WO 97/42966 | 11/1997 |

OTHER PUBLICATIONS

Bristow, et al. "Dose–Response of Chronic β–Blocker Treatment in Heart Failure from Either Idiopathic Dilated or Ischemic Cardiomyopathy" *Circulation* vol 89, No. 4 (1994).

* cited by examiner

*Primary Examiner*—Jean C. Witz
(74) *Attorney, Agent, or Firm*—Marshall, Gerstein & Borun

(57) ABSTRACT

New therapeutic uses for BPI protein products that involve treatment of chronic cardiac disease.

10 Claims, 7 Drawing Sheets

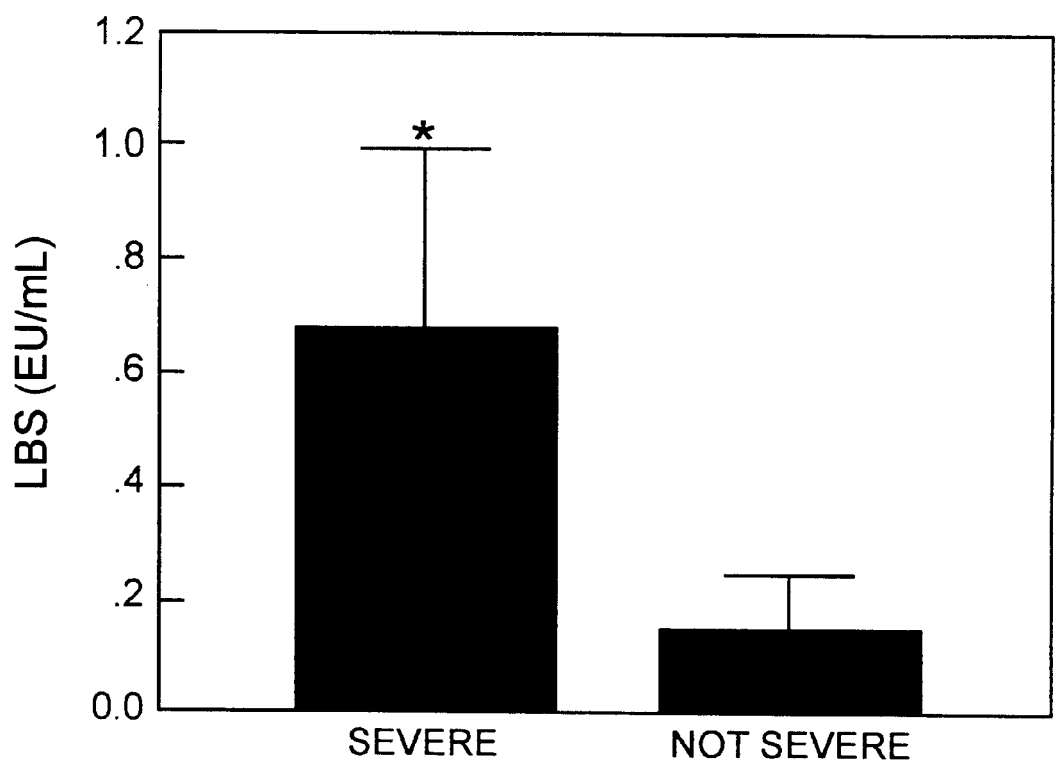

METHOD OF TREATING CHRONIC CARDIAC DISEASE

This application claims priority of U.S. provisional application Serial No. 60/116,736 filed Jan. 22, 1999, the disclosure of which is incorporated herein by reference.

The present invention relates generally to novel therapeutic uses of BPI protein products that involve treatment of chronic cardiac disease including, but not limited to, chronic states such as congestive heart failure and cardiomyopathy.

BACKGROUND OF THE INVENTION

Chronic cardiac disease is a leading cause of mortality and morbidity in the developed world. One type of chronic cardiac disease is cardiomyopathy, which is actually a diverse group of diseases characterized by myocardial dysfunction that is not related to the usual causes of heart disease such as coronary atherosclerosis, valvular dysfunction and hypertension. Cardiomyopathies are categorized hemodynamically into dilated, hypertrophic, restrictive and obliterative cardiomyopathy, and can be of known or idiopathic etiology. Among the etiologies of dilated cardiomyopathy are pregnancy, drugs and toxins, such as alcohol, cocaine and chemotherapeutic agents (including doxorubicin and daunorubicin, dactinomycin, dacarbazine, cyclophosphamide, mitomycin, and anthracycline), and infectious and autoimmune processes. Hypertrophic cardiomyopathy is hereditary in more than 50% of cases and has a distinctive pattern of myocardial hypertrophy (thickening of muscle) usually with a pattern of asymmetrical thickening of the interventricular septum (also called asymmetrical septal hypertrophy). Restrictive cardiomyopathies are usually the product of an infiltrative disease of the myocardium, such as amyloidosis, hemochromatosis or a glycogen storage disease, and may also be seen in certain diabetic patients. Obliterative cardiomyopathy can be caused by endomyocardial fibrosis and hypereosinophilic syndrome. A common complication of all of the cardiomyopathies is progressive congestive heart failure.

Congestive heart failure is often defined as the inability of the heart to deliver a supply of oxygenated blood sufficient to meet the metabolic needs of peripheral tissues at normal filling pressures. Chronic congestive heart failure can result as a consequence of coronary artery disease, cardiomyopathy, myocarditis, aortic stenosis, hypertension, idiopathic asymmetrical septal hypertrophy, coarctation of the aorta, aortic regurgitation, mitral regurgitation, left-to-right shunts, hypertrophied muscle, pericardial tamponade, constrictive pericarditis, mitral stenosis, left atrial mzxoma, left atrial thrombus, cor triatriatum and numerous other conditions. Congestive heart failure is generally distinguished from other causes of inadequate oxygen delivery, such as circulatory collapse from hemorrhage or other causes of severe volume loss, congestion caused by fluid overload and high-output failure caused by increased peripheral demands which occurs in conditions such as thyrotoxicosis, arteriovenous fistula, Paget's disease and anemia. Therapy for congestive heart failure typically focuses on the treating the underlying etiology and the symptoms of fluid overload and heart failure. Chronic congestive heart failure that persists after correction of reversible causes is treated with diuretics (including thiazides such as chlorothiazide and hydrochlorothiazide, loop diuretics such as ethacrynic acid, furosemide, torsemide and bumetanide, potassium sparing agents such as spironolactone, triamterene and amiloride, and others such as metolazone and other quinazoline-sulfonamides), vasodilators (including nitroglycerin, isosorbide dinitrate, hydralazine, sodium nitroprusside, prostacyclin, captopril, enalapril, lisinopril, quinapril and losartan), positive inotropic agents (such as digitalis or digoxin), occasionally beta blockers, or combinations of these measures.

Recent studies indicate that an increase in pro-inflammatory cytokines is seen in diverse cardiac diseases, including congestive heart failure, cardiomyopathy, and myocarditis. Hegewisch S, et al. *Lancet* 1990;2:294–295; Levine B, et al., *N.Engl.Med.* 1990;323 (4):236–241; Mann D L, et al., *Chest* 1994;105:897–904; and Givertz M M, et al., *Lancet* 1998;352:34–38 For example, the cytokine tumor necrosis factor-α(TNF) is synthesized by human cardiac myocytes, and the level of TNF expression correlates with the degree of cardiac dysfunction in patients. Torre-Amione G, et al., *J. Am. Col. Cardiol.* 1996;27:1201–1206; Torre-Amione G, R D, et al. *Circulation* 1995;92:1487–1493; and Torre-Amione G, et al., *Circulation* 1996;93:704–711 In animals, synthesis of TNF by the heart is itself sufficient to cause cardiomyopathy and lethal cardiac failure. Bryant D, et al., *Circ.* 1998;97:175–183 and Kubota T, et al. *J.Am-.Col.Cardiol.* 1997;346A(Abstract) Furthermore, early human trials have demonstrated that antagonism of TNF improves cardiac failure in humans with NYHA Class III heart failure or idiopathic dilated cardiomyopathy. Deswal et al., *Circulation* 96: I-323 (1997); and Sliwa et al., *Lancet* 351: 1091–1093 (1998) However, the primary stimulus for cytokine secretion remains unknown.

Bacterial endotoxin, or lipopolysaccharide (LPS), is a primary inducer of TNF production during sepsis. With respect to cardiac diseases, the role of endotoxin has been examined primarily in the context of cardiopulmonary bypass, driven by the hypothesis that endotoxin may be present in the extracorporeal circuit, or may be translocated across the intestine secondary to non-pulsatile, low flow perfusion. Riddington D W, et al. *JAMA* 1996;275:1007–1012 and Wan S, et al., *Chest* 1997;112:676–692 These studies have demonstrated only transient low-level endotoxemia during cardiopulmonary bypass, with rapid resolution following completion of cardiopulmonary bypass in the majority of patients. Nilsson L, *J Thorac Cardiovasc Surg* 1990;100:777–780; Casey W F, *Crit.Care Med.* 1992;20 (8):1090–1096; Khabar K S, et al., *Clin Immunol Immunopathol* 1997;85:97–103; Jansen N J, *Ann Thorac Surg* 1992;54:744–747. Bennett-Guerrero E et al., *JAMA* 1997;277:646–650 reported that lower levels of anti-endotoxin antibodies pre-operatively were associated with an increased risk of post-operative complications and hypothesized that this difference was Investigators have thus far failed to demonstrate, or failed to attempt to demonstrate, persistent endotoxemia in a majority of patients with cardiac disease Nilsson L,*J Thorac Cardiovasc Surg* 1990; 100:777–780; Casey W F, *Crit. Care Med. 1992;20* (8): 1090–1096; Khabar K S, et al., *Clin Immunol Immunopathol* 1 997;85:97–103; Jansen N J, *Ann Thorac Surg* 1992;54:744–747. See also Niebauer J, *Eur. Heart J.* 1998;19:174, which reported elevated levels of plasma endotoxin in adults with edemetous chronic congestive heart failure that was not associated with elevated levels of LBP or anti-endotoxin antibodies (indicators of long-term endotoxin exposure).

BPI is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.,*

254:11000 (1979)] or *E. coli* affinity chromatography [Weiss, et al., *Blood,* 69:652 (1987)]. BPI obtained in such a manner is referred to herein as natural BPI and has been shown to have potent bactericidal activity against a broad spectrum of gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of Gray et al., *J Biol. Chem.,* 264:9505 (1989), incorporated herein by reference. The Gray et al. amino acid sequence is set out in SEQ ID NO: 1 hereto. U.S. Pat. No. 5,198,541 discloses recombinant genes encoding and methods for expression of BPI proteins, including BPI holoprotein and fragments of BPI.

BPI is a strongly cationic protein. The N-terminal half of BPI accounts for the high net positive charge; the C-terminal half of the molecule has a net charge of –3. [Elsbach and Weiss (1981), supra.] A proteolytic N-terminal fragment of BPI having a molecular weight of about 25 kD possesses essentially all the anti-bacterial efficacy of the naturally-derived 55 kD human BPI holoprotein. [Ooi et al., *J. Bio. Chem.,* 262: 14891–14894 (1987)]. In contrast to the N-terminal portion, the C-terminal region of the isolated human BPI protein displays only slightly detectable anti-bacterial activity against gram-negative organisms. [Ooi et al., *J Exp. Med.,* 174:649 (1991).] An N-terminal BPI fragment of approximately 23 kD, referred to as "rBPI$_{23}$," has been produced by recombinant means and also retains anti-bacterial activity against gram-negative organisms. [Gazzano-Santoro et al., *Infect. Immun.* 60:4754–4761 (1992).] An N-terminal analog of BPI, rBPI$_{21}$, has been produced as described in Horwitz et al., *Protein Expression Purification,* 8:28–40 (1996).

The bactericidal effect of BPI was originally reported to be highly specific to gram-negative species, e.g., in Elsbach and Weiss, *Inflammation: Basic Principles and Clinical Correlates,* eds. Gallin et al., Chapter 30, Raven Press, Ltd. (1992). The precise mechanism by which BPI kills gram-negative bacteria is not yet completely elucidated, but it is believed that BPI must first bind to the surface of the bacteria through electrostatic and hydrophobic interactions between the cationic BPI protein and negatively charged sites on LPS. In susceptible gram-negative bacteria, BPI binding is thought to disrupt LPS structure, leading to activation of bacterial enzymes that degrade phospholipids and peptidoglycans, altering the permeability of the cell's outer membrane, and initiating events that ultimately lead to cell death. [Elsbach and Weiss (1992), supra]. LPS has been referred to as "endotoxin" because of the potent inflammatory response that it stimulates, i.e., the release of mediators by host inflammatory cells which may ultimately result in irreversible endotoxic shock. BPI binds to lipid A, reported to be the most toxic and most biologically active component of LPS.

BPI protein products have a wide variety of beneficial activities. BPI protein products are bactericidal for gram-negative bacteria, as described in U.S. Pat. Nos. 5,198,541 and 5,523,288, both of which are incorporated herein by reference. International Publication No. WO 94/20130 (incorporated herein by reference) proposes methods for treating subjects suffering from an infection (e.g. gastrointestinal) with a species from the gram-negative bacterial genus Helicobacter with BPI protein products. BPI protein products also enhance the effectiveness of antibiotic therapy in gram-negative bacterial infections, as described in U.S. Pat. No. 5,523,288 and International Publication No. WO 95/08344 (PCT/US94/11255), which are incorporated herein by reference. BPI protein products are also bactericidal for gram-positive bacteria and mycoplasma, and enhance the effectiveness of antibiotics in gram-positive bacterial infections, as described in U.S. Pat. Nos. 5,578,572 and 5,783,561 and International Publication No. TWO 95/19180 (PCT/US95/00656), which are incorporated herein by reference. BPI protein products exhibit anti-fungal activity, and enhance the activity of other anti-fungal agents, as described in U.S. Pat. No. 5,627,153 and International Publication No. TWO 95/19179 (PCT/US95/00498), and further as described for anti-fungal peptides in U.S. Pat. No. 5,858,974, which is in turn a continuation-in-part of U.S. application Ser. No. 08/504,841 filed Jul. 20, 1994 and corresponding International Publication Nos. WO 96/08509 (PCT/US95/09262) and WO 97/04008 (PCT/US96/03845), all of which are incorporated herein by reference. BPI protein products exhibit anti-protozoan activity, as described in U.S. Pat. No. 5,646,114 and International Publication No. WO 96/01647 (PCT/US95/08624), which are incorporated herein by reference. BPI protein products exhibit anti-chlamydial activity, as described in co-owned, co-pending U.S. application Serial No. 08/694,843 filed Aug. 9, 1996 and WO 98/06415 (PCT/US97/13810), which are incorporated herein by reference. Finally, BPI protein products exhibit anti-mycobacterial activity, as described in co-owned, co-pending U.S. application Ser. No. 08/626,646 filed Apr. 1, 1996, which is in turn a continuation of U.S. application Ser. No.08/285,803 filed Aug. 14, 1994, which is in turn a continuation-in-part of U.S. application Ser. No. 08/031,145 filed Mar. 12, 1993 and corresponding International Publication No. W094/20129 (PCT/US94/02463), all of which are incorporated herein by reference.

The effects of BPI protein products in humans with endotoxin in circulation, including effects on TNF, IL-6 and endotoxin are described in U.S. Pat. No. 5,643,875, which is incorporated herein by reference.

BPI protein products are also useful for treatment of specific disease conditions, such as meningococcemia in humans (as described in co-owned, co-pending U.S. application Ser. No. 08/644,287 filed May 10, 1996 and continuation No. 08/927,437 filed Sep. 10, 1997 and International Publication No. W097/42966 (PCT/US97/08016), all of which are incorporated herein by reference), hemorrhagic trauma in humans, (as described in U.S. Pat. No. 5,756,464, U.S. application Ser. No. 08/862,785 filed May 23, 1997 and corresponding International Publication No. TWO 97/44056 (PCT/US97/08941), all of which are incorporated herein by reference), burn injury (as described in U.S. Pat. No. 5,494,896, which is incorporated herein by reference), ischemia/reperfusion injury (as described in U.S. Pat. No. 5,578,568, incorporated herein by reference), and liver resection (as described in co-owned, co-pending U.S. application Ser. No. 08/582,230 filed Jan. 3, 1996, which is in turn a continuation of U.S. application Ser. No. 08/318,357 filed Oct. 5, 1994, which is in turn a continuation-in-part of U.S. application Ser. No. 08/132,510 filed Oct. 5, 1993, and corresponding International Publication No. WO 95/10297 PCT/US94/11404), all of which are incorporated herein by reference).

BPI protein products also neutralize the anti-coagulant activity of exogenous heparin, as described in U.S. Pat. No. 5,348,942, incorporated herein by reference, and are useful for treating chronic inflammatory diseases such as rheumatoid and reactive arthritis and for inhibiting angiogenesis and for treating angiogenesis-associated disorders including malignant tumors, ocular retinopathy and endometriosis, as described in U.S. Pat. Nos. 5,639,727, 5,807,818 and 5,837,678 and International Publication No. WO 94/20128 (PCT/US94/02401), all of which are incorporated herein by reference.

BPI protein products are also useful in antithrombotic methods, as described in U.S. Pat. No. 5,741,779 and U.S. application Ser. No. 09/063,465 filed Apr. 20, 1998 and corresponding WO 97/42967 (PCT/US7/08017), all of which are incorporated herein by reference.

SUMMARY OF THE INVENTION

The present invention provides novel therapeutic uses for BPI protein products that involve treatment of subjects with chronic cardiac disease. Uses of BPI protein products according to the invention are specifically contemplated for prophylactic or therapeutic treatment of chronic cardiac disease states or conditions in humans, particularly humans with chronic cardiac disease who exhibit elevated levels of circulating LPS and circulating LBP (in plasma or serum). Chronic cardiac disease states or conditions include but are not limited to cardiomyopathies, chronic congestive heart failure, and congenital heart defects.

Chronic congestive heart failure as used herein includes long-term congestive heart failure (i.e., congestive heart failure persisting more than two weeks, or more than three weeks, or more than one month, or more than two months, or more than three months), congestive heart failure that persists after correction of reversible causes, and congestive heart failure not immediately associated with an acute myocardial infarction or an acute infectious process.

Congenital heart defects, which may result in congestive heart failure or cyanotic heart disease, include pulmonary atresia, total anomalous pulmonary venous return, ventricular septal defect, hypoplastic left heart syndrome, double outlet right ventricle, right pulmonary artery stenosis, interrupted aortic arch, Ebsteins's anomaly, tetralogy of Fallot, atrioventricular canal, transposition of the great arteries and truncus arteriosus.

It is contemplated that the administration of a BPI protein product may be accompanied by the concurrent administration of other known therapeutic agents for treating the chronic cardiac disease state. For example, agents that are known in the art for treating congestive heart failure include diuretics (including thiazides such as chlorothiazide, hydrochlorothiazide and metolazone, loop diuretics such as ethacrynic acid, furosemide, torsemide and bumetanide and their congeners, potassium sparing agents such as spironolactone, canrenone, triamterene and amiloride, and others such as metolazone and other quinazoline-sulfonamides), vasodilators (including nitrovasodilators such as nitroglycerin, isosorbide dinitrate, and sodium nitroprusside, hydralazine, prostacyclin, ACE inhibitors such as captopril, enalapril, lisinopril, quinapril and ramipril, and angiotensin II antagonists such as losartan), positive inotropic agents (such as cardiac glycosides, including digitalis or digoxin), phosphodiesterase inhibitors (such as amrinone and milrinone, primarily useful for short term support), occasionally beta-adrenergic receptor antagonists (beta blockers such as propanolol, metoprolol, atenolol, pindolol, acebutolol, labetalol, carvedilol and celiprolol), or combinations of these measures. See, e.g., Goodman and Gilman, Ch. 34, The Pharmacological Basis of Therapeutics, McGraw Hill, N.Y. (1996), incorporated by reference herein.

The invention also contemplates use of a BPI protein product in the preparation of a medicament for the prophylactic or therapeutic treatment of a chronic cardiac disease state.

Numerous additional aspects and advantages of the invention will become apparent to those skilled in the art upon consideration of the following detailed description of the invention which describes presently preferred embodiments thereof.

DESCRIPTION OF THE DRAWINGS

FIGS. 4A and 4B displays pre-operative plasma LPS (FIG. 4B) and LBP (FIG. 4A) levels in patients with a severe (n=1 5), versus less severe (n=15), post-operative clinical course.

DETAILED DESCRIPTION OF THE INVENTION

Figure 1A:
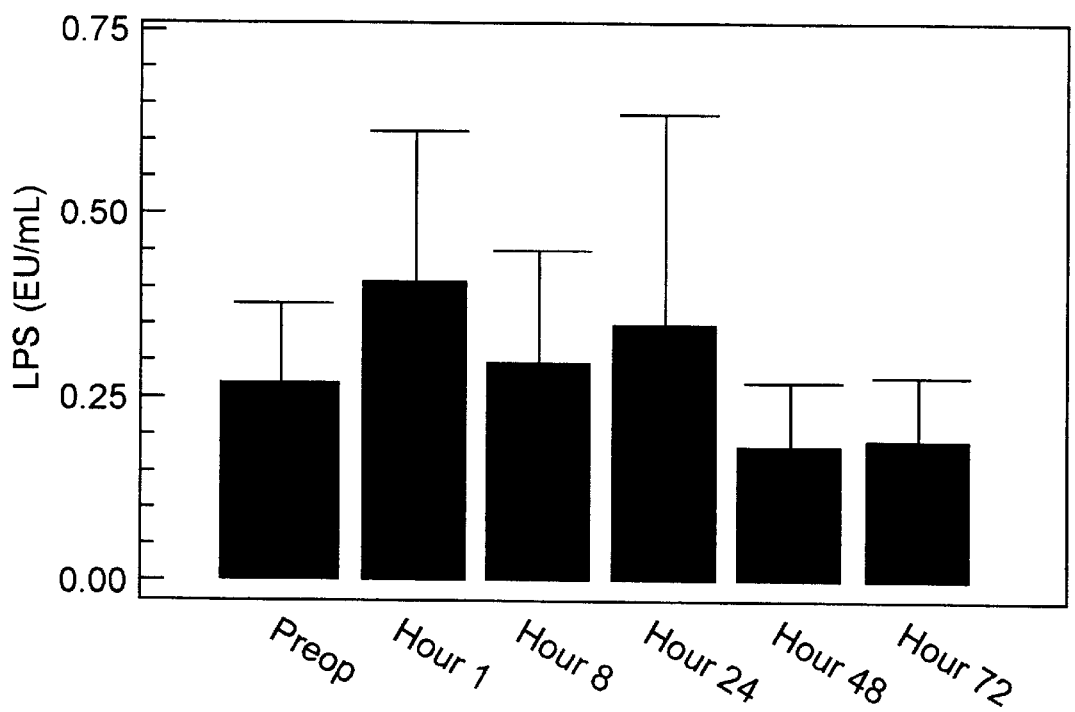
FIG. 1A displays plasma LPS levels for all patients completing the study protocol (n=29).

The present invention provides novel therapeutic uses for BPI protein products, particularly BPI-derived peptides, that involve treatment of chronic cardiac disease. "Treatment" as used herein encompasses both prophylactic and therapeutic treatment. The invention contemplates methods for treatment of subjects suffering from chronic heart disease which comprise the administration of therapeutically effective amounts of bactericidal/permeability-increasing protein (BPI) protein products to those subjects so as to alleviate the negative physiological effects of endotoxemia.

The invention is based on the discovery that a substantial proportion of subjects suffering from chronic heart disease exhibit evidence of endotoxemia associated with the chronic heart disease prior to surgery, and that this endotoxemia correlates to a poorer prognosis for these subjects. Thus, one basis for the invention is the expectation that endotoxemia is not simply a side effect of chronic cardiac disease but is a significant contributing factor to the pathology of chronic cardiac disease.

Therapeutic uses of BPI protein products are specifically contemplated for treatment of mammals, including humans, suffering from chronic cardiac disease as distinguished from acute cardiac disease states such as myocardial infarction, circulatory collapse from hemorrhage and the like.

Another aspect of the present invention is the treatment of patients undergoing cardiopulmonary bypass, on the basis that the severity of endotoxemia during and after cardiopulmonary bypass is correlated with poorer post-surgical outcome. Thus, treatment with BPI protein product is expected to improve post-surgical outcome.

As used herein, "BPI protein product" includes naturally and recombinantly produced BPI protein; natural, synthetic, and recombinant biologically active polypeptide fragments of BPI protein; biologically active polypeptide variants of BPI protein or fragments thereof, including hybrid fusion proteins and dimers; biologically active polypeptide analogs of BPI protein or fragments or variants thereof, including cysteine-substituted analogs; and BPI-derived peptides. The BPI protein products administered according to this invention may be generated and/or isolated by any means known in the art. U.S. Pat. No. 5,198,541, the disclosure of which is incorporated herein by reference, discloses recombinant genes encoding, and methods for expression of, BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed mammalian host cells in culture and discloses how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein. Nonlimiting examples of such fragments include an N-terminal fragment of natural human BPI of approximately 25 kD, described in Ooi et al., *J. Exp. Med.,* 174:649 (1991), and the recombinant expression product of DNA encoding N-terminal amino acids from 1 to about 193 to 199 of natural human BPI, described in Gazzano-Santoro et al., *Infect. Immun.* 60:4754–4761 (1992), and referred to as rBPI$_{23}$. In that publication, an expression vector was used as a source of DNA encoding a recombinant expression product (rBPI$_{23}$) having the 31-residue signal sequence and the first 199 amino acids of the N-terminus of the mature human BPI, as set out in FIG. 1 of Gray et al., supra, except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of Gray et al., supra, with the exceptions noted for rBPI$_{23}$ and with the exception that residue 417 is alanine (specified by GCT) rather than valine (specified by GTT). A fragment consisting of residues 10–193 of BPI has been described in co-owned, co-pending U.S. application Ser. No. 09/099,725 filed Jun. 19, 1998, incorporated herein by reference. Other examples include dimeric forms of BPI fragments, as described in U.S. Pat. No. 5,447,913 and corresponding International Publication No. WO 95/24209 (PCT/US95/03125), all of which are incorporated herein by reference.

Biologically active variants of BPI (BPI variants) include but are not limited to recombinant hybrid fusion proteins, comprising BPI holoprotein or biologically active fragment thereof and at least a portion of at least one other polypeptide, and dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. No. 5,420,019 and corresponding International Publication No. WO 94/18323 (PCT/US94/01235), all of which are incorporated herein by reference, discloses polypeptide analogs of BPI and BPI fragments wherein a cysteine residue is replaced by a different amino acid. A stable BPI protein product described by this application is the expression product of DNA encoding from amino acid 1 to approximately 193 or 199 of the N-terminal amino acids of BPI holoprotein, but wherein the cysteine at residue number 132 is substituted with alanine and is designated rBPI$_{21}\Delta$cys or rBPI$_{21}$. Production of this N-terminal analog of BPI, rBPI$_{21}$, has been described in Horwitz et al., *Protein Expression Purification,* 8:28–40 (1996). Similarly, a fragment consisting of residues 10–193 of BPI in which the cysteine at position 132 is replaced with an alanine (designated "rBPI(10–193)C132A" or "rBPI(10–193)ala$^{32}$") has been described in co-owned, co-pending U.S. application Ser. No. 09/099,725 filed Jun. 19, 1998. Other examples include dimeric forms of BPI analogs; e.g. U.S. Pat. No. 5,447,913 and corresponding International Publication No. WO 95/24209 (PCT/US95/03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. No. 5,652,332, and International Publication No. WO94/20532 (PCT/US94/02465), which corresponds to U.S. Pat. No. 5,763,567 which is a continuation of U.S. Pat. No. 5,733,872, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference.

Presently preferred BPI protein products include recombinantly-produced N-terminal analogs and fragments of BPI, especially those having a molecular weight of approximately between 20 to 25 kD such as rBPI$_2$, or rBPI$_{23}$, rBPI(10–193)C132A (rBPI(10–193)ala$^{32}$), dimeric forms of these N-terminal proteins (e.g., rBPI$_{42}$ dimer), and BPI-derived peptides.

The administration of BPI protein products is preferably accomplished with a pharmaceutical composition comprising a BPI protein product and a pharmaceutically acceptable diluent, adjuvant, or carrier. The BPI protein product may be administered without or in conjunction with known surfactants or other therapeutic agents. A stable pharmaceutical composition containing BPI protein products (e.g., rBPI$_{23}$) comprises the BPI protein product at a concentration of 1 mg/ml in citrate buffered saline (5 or 20 mM citrate, 150 mM NaCl, pH 5.0) comprising 0.1 % by weight of poloxamer 188 (Pluronic F-68, BASF Wyandotte, Parsippany, N.J.) and 0.002% by weight of polysorbate 80 (Tween 80, ICI Americas Inc., Wilmington, Del.). Another stable pharmaceutical composition containing BPI protein products (e.g., rBPI$_{21}$,) comprises the BPI protein product at a concentration of 2 mg/ml in 5 mM citrate, 150 mM NaCl, 0.2% poloxamer 188 and 0.002% polysorbate 80. Such preferred combinations are described in U.S. Pat. Nos. 5,488,034 and 5,696,090 and corresponding International Publication No. WO 94/17819 (PCT/US94/01239), the disclosures of all of which are incorporated herein by reference. As described in U.S. application Ser. No. 08/586,133 filed Jan. 12, 1996, which is in turn a continuation-in-part-of U.S. application Ser. No. 08/530,599 filed Sep. 19,1995, which is in turn a continuation-in-part of U.S. application Ser. No. 08/372,104 filed Jan. 13, 1995, and corresponding International Publication No. WO96/21436 (PCT/US96/01095), all of which are incorporated herein by reference, other poloxamer formulations of BPI protein products with enhanced activity may be utilized.

Therapeutic compositions comprising BPI protein product may be administered systemically or topically. Systemic routes of administration include oral, intravenous, intramuscular or subcutaneous injection (including into a depot for long-term release), intraocular and retrobulbar, intrathecal, intraperitoneal (e.g. by intraperitoneal ravage), intrapulmonary (using powdered drug, or an aerosolized or nebulized drug solution), or transdermal.

When given parenterally, BPI protein product compositions are generally injected in doses ranging from 1 $\mu$g/kg to 100 mg/kg per day, preferably at doses ranging from 0.1 mg/kg to 20 mg/kg per day, more preferably at doses ranging from 1 to 20 mg/kg/day and most preferably at doses ranging from 2 to 10 mg/kg/day. The treatment may continue by continuous infusion or intermittent injection or infusion, at the same, reduced or increased dose per day for, e.g., 1 to 3 days, and additionally as determined by the treating physician. When administered intravenously, BPI protein products are preferably administered by an initial brief infusion followed by a continuous infusion. The preferred intravenous regimen is a 1 to 20 mg/kg brief intravenous infusion of BPI protein product followed by a continuous intravenous infusion at a dose of 1 to 20 mg/kg/day, continuing for up to one week. A particularly preferred intravenous dosing regimen is a 1 to 4 mg/kg initial brief intravenous infusion followed by a continuous intravenous infusion at a dose of 1 to 4 mg/kg/day, continuing for up to 72 hours.

Those skilled in the art can readily optimize effective dosages and administration regimens for therapeutic compositions comprising BPI protein product, as determined by good medical practice and the clinical condition of the individual patient.

"Concurrent administration," or "co-administration," as used herein includes administration of the agents, in conjunction or combination, together, or before or after each other. The BPI protein product and second agent(s) may be administered by different routes. For example, the BPI protein product may be administered intravenously while the second agent(s) is(are) administered intravenously, intramuscularly, subcutaneously, orally or intraperitoneally. The BPI protein product and second agent(s) may be given sequentially in the same intravenous line or may be given in different intravenous lines. Alternatively, the BPI protein product may be administered in a special form for gastric delivery, while the second agent(s) is(are) administered, e.g., orally. The formulated BPI protein product and second agent(s) may be administered simultaneously or sequentially, as long as they are given in a manner sufficient to allow all agents to achieve effective concentrations at the site of action.

Other aspects and advantages of the present invention will be understood upon consideration of the following illustrative examples. Example 1 addresses a study in which thirty children with complex chronic heart disease were tested for markers of endotoxemia prior to and at 1, 8, 24, 48 and 72 hours following cardiopulmonary bypass surgery.

EXAMPLE 1

The experimental protocol, approved by the Institutional Review Board at the University of Texas Southwestern Medical Center, was an unblinded, prospective study in which 30 children with severe congenital heart disease were sequentially enrolled while awaiting surgical repair and/or palliation. One patient with hypoplastic left heart syndrome died intra-operatively, and therefore data on this child are included only in the pre-operative analysis. Patients with clinical evidence of preoperative infection were excluded from the study.

The 30 enrolled children ranged in age from 4 days to 402 days (median age 59 days), and in weight from 2.0 to 9.5 kg (median weight 4.0 kg) The genders, ages, cardiac diagnoses, and surgical repairs are listed in Table 1 below.

TABLE 1

Patient Characteristics

| Sex | Age-days | Wt (kg) | Diagnosis* | Procedure |
|---|---|---|---|---|
| M | 349 | 8.90 | Pulmonary Atresia | RVOT Reconstruction |
| M | 6 | 5.70 | TAPVR | TAPVR Repair |
| F | 265 | 6.60 | TAPVR | TAPVR Repair |
| M | 5 | 3.30 | Interrupted Aortic Arch | Aortic Arch Repair |
| M | 44 | 3.50 | Ebstein's anomaly, VSD | VSD Repair |
| M | 245 | 8.09 | VSD | VSD Repair |
| F | 7 | 2.50 | HLHS | Norwood Procedure |
| F | 10 | 3.4 | HLHS | Norwood Procedure |
| F | 210 | 6.70 | VSD | VSD Repair |
| M | 163 | 5.00 | DORV, RPA Stenosis | DKS |
| F | 395 | 8.20 | TOF | Tetralogy Repair |
| M | 10 | 2.50 | TGA, DORV | Arterial Switch |
| M | 75 | 3.60 | AV Canal | AV Canal Repair |
| M | 4 | 4.40 | TGA | Arterial Switch |
| M | 4 | 3.60 | TGA | Arterial Switch |
| M | 4 | 3.35 | LV Rhabdomyosarcoma | Tumor Resection |
| M | 26 | 3.70 | TAPVR | TAPVR Repair |
| F | 110 | 3.20 | TAPVR | TAPVR Repair |
| F | 126 | 2.00 | Truncus Arteriosus | RVOT Reconstruction |
| M | 402 | 9.50 | TOF | Tetralogy Repair |
| M | 25 | 2.60 | Pulmonary Atresia | RVOT Reconstruction |
| F | 105 | 4.40 | AV Canal | AV Canal Repair |
| M | 178 | 5.80 | TOF | Tetralogy Repair |
| M | 5 | 4.40 | TGA | Arterial Switch |
| M | 102 | 4.10 | TAPVR | TAPVR Repair |
| F | 5 | 3.70 | TAPVR | TAPVR Repair |
| M | 6 | 3.10 | HLHS | Norwood Procedure |
| F | 120 | 5.40 | AV Canal | AV Canal Repair |
| M | 4 | 3.80 | TGA | Arterial Switch |
| M | 335 | 7.50 | TOF | Tetralogy Repair |

*RVOT-right ventricular outflow tract; TAPVR-total anomalous pulmonary venous return; VSD-ventricular septal defect; HLHS-hypoplastic left heart syndrome; DORV-double outlet right ventricle; RPA-right pulmonary artery; DKS-Damus-Kaye-Stansel shunt operation; TOF-tetralogy of Fallot; AV canal-atrioventricular canal; TGA-transposition of the great arteries.

Anesthesia was induced with sevoflurane, nitrous oxide and oxygen; intubation was facilitated with intravenous rocuronium and fentanyl. Anesthesia was maintained with fentanyl (30–50 mcg/kg), isoflurane, and pancuronium. Nine patients received tranexamic acid (50–100 mg/kg) and 3 received aprotinin (dosed to achieve 350 units/mL total blood volume).

Cardiopulmonary bypass was performed as follows. The extracorporeal circuit consisted of a roller pump, membrane oxygenator, and cardiotomy filters Prior to the institution of cardiopulmonary bypass, the patients' blood was anticoagulated with heparin (300 units/kg). 13 patients underwent deep hypothermic circulatory arrest (core temp 16–18° C.) and the remainder were cooled to a core temperature of 25–30° C. for the completion of surgery. Hemofiltration was performed prior to completion of cardiopulmonary bypass on all patients in an attempt to remove excess free water and attain a hemoglobin >12 gm/dL.

Blood samples for the determination of LPS, LBP, and IL-6 were obtained prior to surgery and at 1, 8, 24, 48 and 72 hours after completion of cardiopulmonary bypass. The pre-operative sample was obtained from a newly placed central venous catheter, immediately after the induction of anesthesia and endotracheal intubation. For determination of endotoxin levels, blood samples were collected into heparinized Vacutainer™ tubes (Becton-Dickson, Rutherford N.J.) selected for low endotoxin content (Bio Whitaker, Walkersville, Md.), immediately placed on ice, and walked to the laboratory by an investigator. Platelet-rich plasma was obtained by centrifigation (180×g, 10 min, 2–8° C.). Samples were stored at −70° C. until assay.

LPS, LBP and IL-6 assays were conducted in a blinded fashion. The level of LPS in the platelet-rich plasma was determined by using a kinetic chromogenic Limulus amebocyte lysate assay (Endochrome-K™, Endosafe, Charleston, S.C.) according to the manufacturer's instructions. LPS concentrations are expressed in terms of endotoxin units (EU) per ml relative to an *E. coli* 055:B5 control standard endotoxin. LBP levels were determined by ELISA as described in Meszaros S, et al., *Infect.Immun.* 1995;63:363–365. IL-6 was measured using a sandwich ELISA (R&D Systems, Minneapolis).

A severe (versus less-severe) post operative course was prospectively defined. Severity of post-operative myocardial dysfunction was estimated according to an adaptation of the scale utilized by Weonovsky et al., *Circulation* 1995;92:2226–2235. Specifically, an inotropic support score was calculated as follows: each 1.0 mcglkg/min of dopamine or dobutamine, and each 0.01 mcg/kg/min of epinephrine yielded a score of 1. Children with a net positive fluid balance of >40 cc/kg in the first 24 hours and an inotropic support score of >12, or perioperative death, were considered to have a severe clinical course. Post-operative severity of illness was scored prior to knowledge of LPS, LBP, or IL-6 values.

All statistical analyses were performed on the Statistical Package for the Social Sciences (SPSS). Wilcoxon signed rank tests for non-parametric data were performed to determine if a significant rise in LPS, LBP. or IL-6 had occurred post-operatively. A Mann-Whitney test for non-parametric data was performed to determine if there was a significant difference in LPS or LBP concentrations between the patients who had a more severe clinical course compared to those with a less severe clinical course.

Figure 1B:
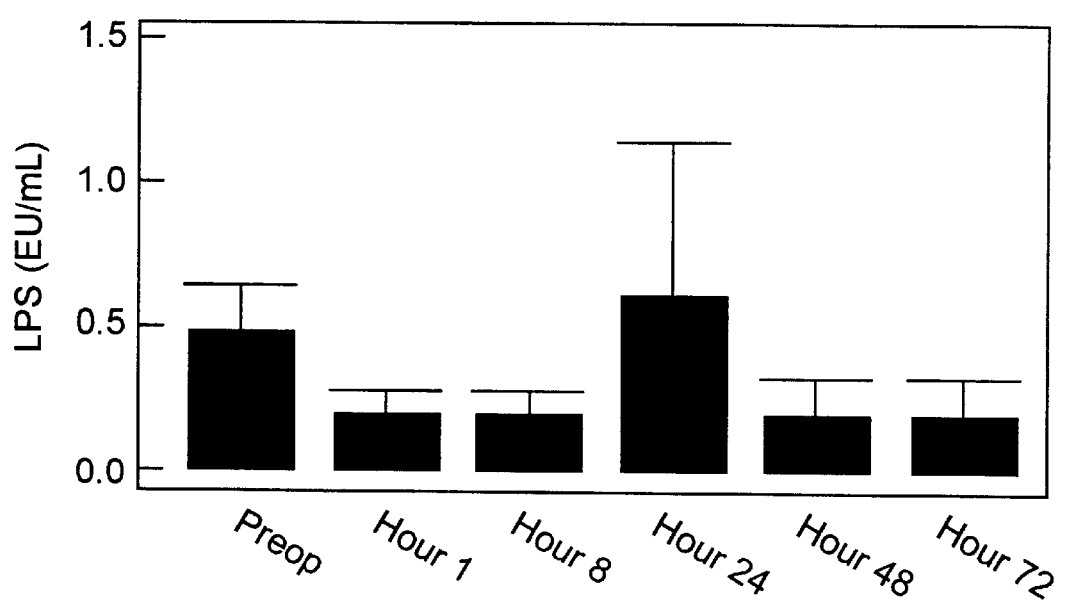
FIG. 1B displays data from patients with endotoxemia pre-operatively (n=11), while FIG. 1C displays data from patients without endotoxemia pre-operatively (n=18).
Figure 1C:
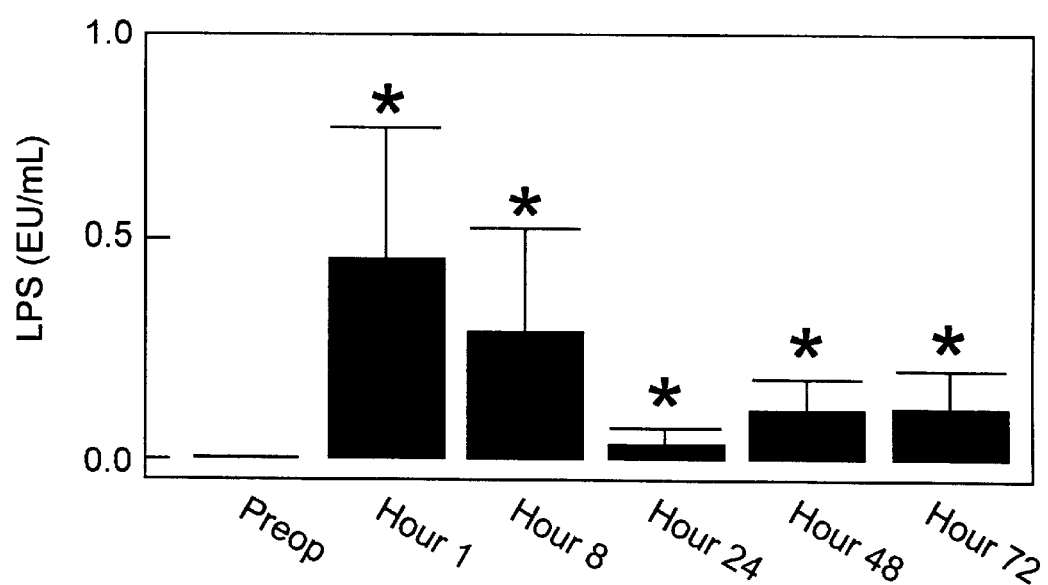
Figure 2:
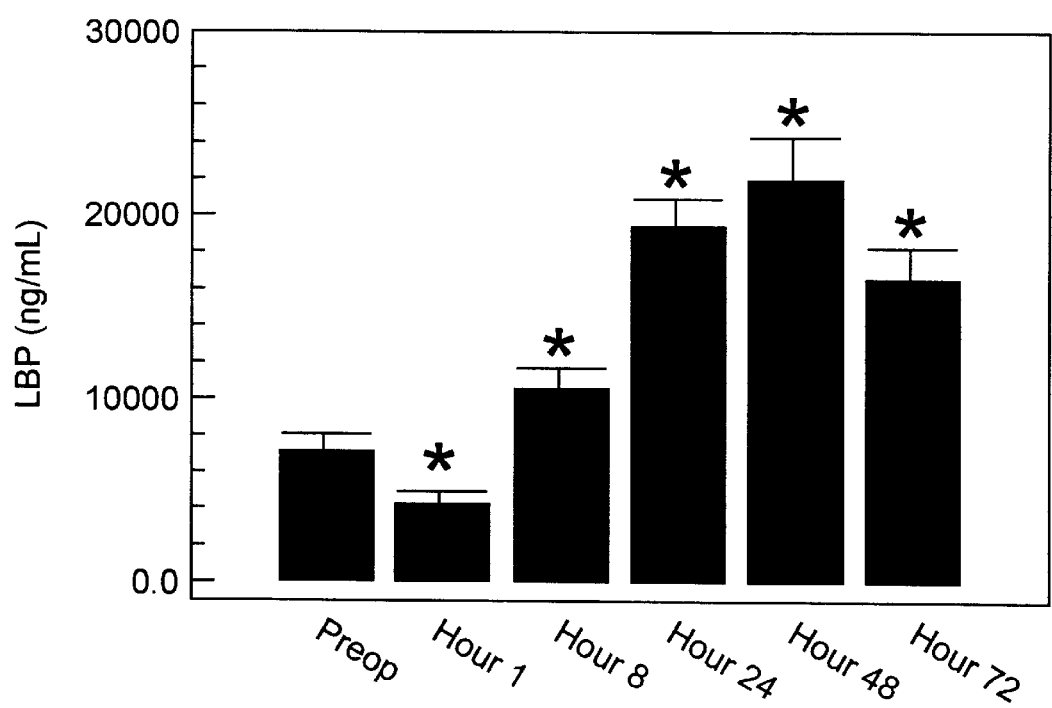
FIG. 2 displays plasma LBP levels from all patients completing the study protocol (n=29).

Twenty-nine of the thirty patients (96%) had evidence of endotoxemia during the study period, either by detection of elevated LPS directly or by detection of an elevated LBP plasma level>2SD above the mean for healthy adults. The LPS, LBP and IL-6 levels for all patients are displayed in FIGS. 1A, 2 and 3. FIG. 1A displays data from all children completing the study protocol and demonstrate elevated LPS at all time points. Differences between pre-operative and post-operative LPS levels are statistically non-significant. To better elucidate endotoxin kinetics, we divided patients into two groups: those who were endotoxemic prior to cardiopulmonary bypass, and those who were not endotoxemic prior to cardiopulmonary bypass (CPB). Levels for these two groups are shown in FIGS. 1B and 1C, respectively.

Prior to CPB, 12 patients had significant elevation of plasma endotoxin. In these patients, endotoxin tended to decline following completion of cardiopulmonary bypass, likely due to hemodilution/partial exchange transfusion (FIG. 1B); but endotoxin levels remained abnormally elevated throughout the study period. In those children without pre-operative endotoxemia, the level of plasma endotoxin rose significantly following bypass, achieving a peak value at 1 hour post bypass, and remaining significantly elevated thereafter (p<0.0001) (FIG. 1C).

Figure 3:
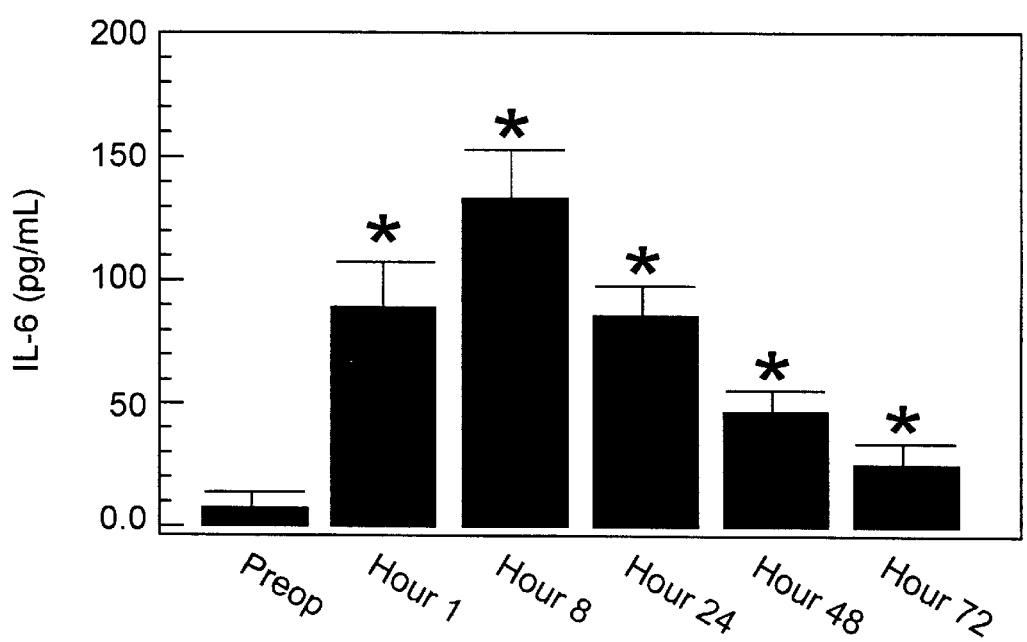
FIG. 3 displays plasma IL-6 levels from all patients completing the study protocol (n=29).

There was a transient, but significant decrease in plasma LBP immediately after completion of cardiopulmonary bypass and hemofiltration. The decrease in plasma LBP at 1 hour following cardiopulmonary bypass was statistically significant (p<0.0001), and the increase in LBP at all points thereafter was also highly consistent and statistically significant (p<0.0001) compared to preoperative levels. This rise in LBP was similar for patients who were and were not endotoxemic preoperatively. Similarly, there was a significant rise in IL-6 at all time points following CPB (p<0.05) compared to preoperative levels (FIG. 3).

Figure 4A:
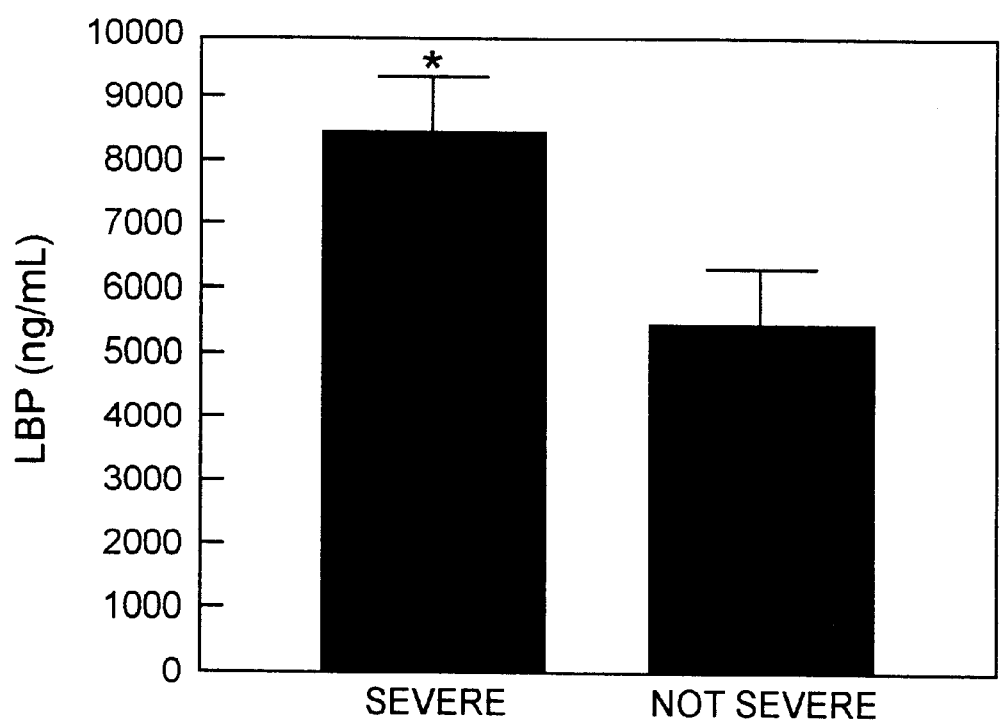

Finally, it was determined whether children who experienced a more severe clinical course, defined prospectively, might differ from less severe patients when pre-operative LPS and LBP levels were compared. In this comparison, the more severely ill children had significantly higher pre-operative plasma LBP (p<0.02) (FIG. 4A), and tended toward higher pre-operative LPS (p<0.05) compared to patients who experienced a less severe post-operative course (FIG. 4B). Additionally, of the 12 patients who were endotoxermic prior to surgery, there were 3 deaths (25%), compared to 0 deaths in the 18 patients who were not endotoxemic prior to surgery (p=0.054).

The underlying biology of pre-operative endotoxemia is clarified by dividing those patients who were or were not endotoxemic-pre operatively. In patients who were endotoxemic pre-operatively, endotoxin levels initially fell following cardiopulmonary bypass, but remained abnormally elevated throughout the study period. This initial decrease may have been secondary to a dilution effect of cardiopulmonary bypass, given the infants' small blood volumes, or perhaps due to clearance of endotoxin by hemofiltration prior to completion of cardiopulmonary bypass. Millar A B, *Ann Thorac Surg* 1993;56:1499–1502 It is also possible that these patients, who were endotoxemic pre-operatively, may have induced and enhanced mechanisms for endotoxin clearance, compared to patients who were not endotoxemic pre-operatively. Dentener M A, et al.,. *Journal of Infectious Diseases* 1997;175:108–117 Dentener M A, *Journal of Infectious Diseases* 1995; 171:739–743; and Gazzano-Santoro et al., *Infect.Immunol.* 1994;62, No4:1185–1191

In contrast, patients who were not endotoxemic pre-operatively demonstrated a significant elevation of plasma endotoxin at one and eight hours after cardiopulmonary bypass. A number of factors have been invoked to explain endotoxemia during cardiopulmonary bypass. First, there are many sources of endotoxin including the extracorporeal circuit, infusion solutions, drugs, and surgical materials. More importantly, increased intestinal permeability during cardiopulmonary bypass has been documented in adult patients, allowing for bacterial translocation and release of endotoxin into the circulation. Measures such as pulsatile perfusion or higher flow during bypass to improve gut perfusion and aggressive antibiotic regimens to decrease intestinal bacterial load prior to bypass have resulted in lower plasma LPS level. Watarida S, et al., *J Thorac Cardiovasc Surg* 1994;108:620–625; and Quigley R L, et al. *Perfusion* 1995;10:27–31.

The finding of elevated LPS and LBP levels pre-operatively in a substantial proportion of children with chronic cardiac disease indicates that endotoxemia is associated with the chronic cardiac disease itself The finding that severity of outcome correlated with endotoxemia as measured by elevated LPS and LBP levels indicates that measurement of endotoxemia can be used to predict prognosis. Consequently, the treatment of endotoxemia with BPI protein product is expected to ameliorate the signs and symptoms of chronic cardiac disease and to improve the prognosis of these patients.

Numerous modifications and variations of the above-described invention are expected to occur to those of skill in the art. Accordingly, only such limitations as appear in the appended claims should be placed thereon.

What is claimed is:

1. A method of treating chronic cardiac disease in a human wherein the human exhibits elevated circulating levels of LPS comprising the step of administering a therapeutically effective amount of a bactericidal/permeability-increasing (BPI) protein product to said human.

2. The method of claim 1 wherein the BPI protein product is rBPI$_{21}$.

3. The method of claim 1 wherein the chronic cardiac disease is chronic congestive heart failure.

4. The method of claim 1 wherein the chronic cardiac disease is cardiomyopathy.

5. The method of claim 1 wherein the chronic cardiac disease is a congenital heart defect.

6. The method of claim 1 wherein the human exhibits elevated levels of circulating LPS.

7. The method of claim 1 wherein the human exhibits elevated levels of circulating LBP.

8. The method of claim 1 wherein the human exhibits elevated levels of circulating LPS and circulating LBP.

9. The method of claim 1 further comprising concurrently administering a second therapeutic agent for treating the chronic cardiac disease state.

10. The method of claim 9 wherein said chronic cardiac disease state is chronic congestive heart failure and the second therapeutic agent is selected from the group consisting of diuretics, positive inotropic agents, vasodilators and beta-blockers.

* * * * *

SEQUENCE LISTING

<160> NUMBER OF SEQ ID NOS: 2

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<220> FEATURE:
<221> NAME/KEY: mat_peptide
<222> LOCATION: (124)..(1491)

<400> SEQUENCE: 1

```
caggccttga ggttttggca gctctggagg atg aga gag aac atg gcc agg ggc        54
                                Met Arg Glu Asn Met Ala Arg Gly
                                 -30                 -25 cct tgc aac gcg ccg aga tgg gtg tcc ctg atg gtg ctc gtc gcc ata       102
Pro Cys Asn Ala Pro Arg Trp Val Ser Leu Met Val Leu Val Ala Ile
        -20                 -15                 -10 ggc acc gcc gtg aca gcg gcc gtc aac cct ggc gtc gtg gtc agg atc       150
Gly Thr Ala Val Thr Ala Ala Val Asn Pro Gly Val Val Val Arg Ile
        -5                 -1   1                  5 tcc cag aag ggc ctg gac tac gcc agc cag cag ggg acg gcc gct ctg       198
Ser Gln Lys Gly Leu Asp Tyr Ala Ser Gln Gln Gly Thr Ala Ala Leu
 10                  15                  20                  25 cag aag gag ctg aag agg atc aag att cct gac tac tca gac agc ttt       246
Gln Lys Glu Leu Lys Arg Ile Lys Ile Pro Asp Tyr Ser Asp Ser Phe
                30                  35                  40 aag atc aag cat ctt ggg aag ggg cat tat agc ttc tac agc atg gac       294
Lys Ile Lys His Leu Gly Lys Gly His Tyr Ser Phe Tyr Ser Met Asp
            45                  50                  55 atc cgt gaa ttc cag ctt ccc agt tcc cag ata agc atg gtg ccc aat       342
Ile Arg Glu Phe Gln Leu Pro Ser Ser Gln Ile Ser Met Val Pro Asn
         60                  65                  70 gtg ggc ctt aag ttc tcc atc agc aac gcc aat atc aag atc agc ggg       390
Val Gly Leu Lys Phe Ser Ile Ser Asn Ala Asn Ile Lys Ile Ser Gly
     75                  80                  85 aaa tgg aag gca caa aag aga ttc tta aaa atg agc ggc aat ttt gac       438
Lys Trp Lys Ala Gln Lys Arg Phe Leu Lys Met Ser Gly Asn Phe Asp
 90                  95                 100                 105 ctg agc ata gaa ggc atg tcc att tcg gct gat ctg aag ctg ggc agt       486
Leu Ser Ile Glu Gly Met Ser Ile Ser Ala Asp Leu Lys Leu Gly Ser
                110                 115                 120 aac ccc acg tca ggc aag ccc acc atc acc tgc tcc agc tgc agc agc       534
Asn Pro Thr Ser Gly Lys Pro Thr Ile Thr Cys Ser Ser Cys Ser Ser
            125                 130                 135 cac atc aac agt gtc cac gtg cac atc tca aag agc aaa gtc ggg tgg       582
His Ile Asn Ser Val His Val His Ile Ser Lys Ser Lys Val Gly Trp
        140                 145                 150 ctg atc caa ctc ttc cac aaa aaa att gag tct gcg ctt cga aac aag       630
Leu Ile Gln Leu Phe His Lys Lys Ile Glu Ser Ala Leu Arg Asn Lys
    155                 160                 165
```

-continued

| | |
|---|---:|
| atg aac agc cag gtc tgc gag aaa gtg acc aat tct gta tcc tcc aag<br>Met Asn Ser Gln Val Cys Glu Lys Val Thr Asn Ser Val Ser Ser Lys<br>170                 175                    180                  185 | 678 |
| ctg caa cct tat ttc cag act ctg cca gta atg acc aaa ata gat tct<br>Leu Gln Pro Tyr Phe Gln Thr Leu Pro Val Met Thr Lys Ile Asp Ser<br>                    190                          195                    200 | 726 |
| gtg gct gga atc aac tat ggt ctg gtg gca cct cca gca acc acg gct<br>Val Ala Gly Ile Asn Tyr Gly Leu Val Ala Pro Pro Ala Thr Thr Ala<br>                205                         210                    215 | 774 |
| gag acc ctg gat gta cag atg aag ggg gag ttt tac agt gag aac cac<br>Glu Thr Leu Asp Val Gln Met Lys Gly Glu Phe Tyr Ser Glu Asn His<br>            220                        225                    230 | 822 |
| cac aat cca cct ccc ttt gct cca cca gtg atg gag ttt ccc gct gcc<br>His Asn Pro Pro Pro Phe Ala Pro Pro Val Met Glu Phe Pro Ala Ala<br>235                 240                         245 | 870 |
| cat gac cgc atg gta tac ctg ggc ctc tca gac tac ttc ttc aac aca<br>His Asp Arg Met Val Tyr Leu Gly Leu Ser Asp Tyr Phe Phe Asn Thr<br>250                 255                    260                    265 | 918 |
| gcc ggg ctt gta tac caa gag gct ggg gtc ttg aag atg acc ctt aga<br>Ala Gly Leu Val Tyr Gln Glu Ala Gly Val Leu Lys Met Thr Leu Arg<br>                    270                         275                    280 | 966 |
| gat gac atg att cca aag gag tcc aaa ttt cga ctg aca acc aag ttc<br>Asp Asp Met Ile Pro Lys Glu Ser Lys Phe Arg Leu Thr Thr Lys Phe<br>            285                        290                    295 | 1014 |
| ttt gga acc ttc cta cct gag gtg gcc aag aag ttt ccc aac atg aag<br>Phe Gly Thr Phe Leu Pro Glu Val Ala Lys Lys Phe Pro Asn Met Lys<br>300                 305                    310 | 1062 |
| ata cag atc cat gtc tca gcc tcc acc ccg cca cac ctg tct gtg cag<br>Ile Gln Ile His Val Ser Ala Ser Thr Pro Pro His Leu Ser Val Gln<br>315                 320                    325 | 1110 |
| ccc acc ggc ctt acc ttc tac cct gcc gtg gat gtc cag gcc ttt gcc<br>Pro Thr Gly Leu Thr Phe Tyr Pro Ala Val Asp Val Gln Ala Phe Ala<br>330                 335                    340                    345 | 1158 |
| gtc ctc ccc aac tcc tcc ctg gct tcc ctc ttc ctg att ggc atg cac<br>Val Leu Pro Asn Ser Ser Leu Ala Ser Leu Phe Leu Ile Gly Met His<br>                    350                         355                    360 | 1206 |
| aca act ggt tcc atg gag gtc agc gcc gag tcc aac agg ctt gtt gga<br>Thr Thr Gly Ser Met Glu Val Ser Ala Glu Ser Asn Arg Leu Val Gly<br>            365                        370                    375 | 1254 |
| gag ctc aag ctg gat agg ctg ctc ctg gaa ctg aag cac tca aat att<br>Glu Leu Lys Leu Asp Arg Leu Leu Leu Glu Leu Lys His Ser Asn Ile<br>380                 385                    390 | 1302 |
| ggc ccc ttc ccg gtt gaa ttg ctg cag gat atc atg aac tac att gta<br>Gly Pro Phe Pro Val Glu Leu Leu Gln Asp Ile Met Asn Tyr Ile Val<br>395                 400                    405 | 1350 |
| ccc att ctt gtg ctg ccc agg gtt aac gag aaa cta cag aaa ggc ttc<br>Pro Ile Leu Val Leu Pro Arg Val Asn Glu Lys Leu Gln Lys Gly Phe<br>410                 415                    420                    425 | 1398 |
| cct ctc ccg acg ccg gcc aga gtc cag ctc tac aac gta gtg ctt cag<br>Pro Leu Pro Thr Pro Ala Arg Val Gln Leu Tyr Asn Val Val Leu Gln<br>                    430                         435                    440 | 1446 |
| cct cac cag aac ttc ctg ctg ttc ggt gca gac gtt gtc tat aaa<br>Pro His Gln Asn Phe Leu Leu Phe Gly Ala Asp Val Val Tyr Lys<br>            445                        450                    455 | 1491 |
| tgaaggcacc aggggtgccg gggctgtca gccgcacctg ttcctgatgg gctgtggggc | 1551 |
| accggctgcc tttccccagg gaatcctctc cagatcttaa ccaagagccc cttgcaaact | 1611 |
| tcttcgactc agattcagaa atgatctaaa cacgaggaaa cattattcat tggaaaagtg | 1671 |

-continued

```
catggtgtgt attttaggga ttatgagctt ctttcaaggg ctaaggctgc agagatattt    1731
cctccaggaa tcgtgtttca attgtaacca agaaatttcc atttgtgctt catgaaaaaa    1791
aacttctggt tttttcatg tg                                              1813
```

<210> SEQ ID NO 2
<211> LENGTH: 487
<212> TYPE: PRT
<213> ORGANISM: Homo sapiens

<400> SEQUENCE: 2

```
Met Arg Glu Asn Met Ala Arg Gly Pro Cys Asn Ala Pro Arg Trp Val
    -30                 -25                 -20

Ser Leu Met Val Leu Val Ala Ile Gly Thr Ala Val Thr Ala Ala Val
-15                 -10                  -5              -1   1

Asn Pro Gly Val Val Arg Ile Ser Gln Lys Gly Leu Asp Tyr Ala
                  5                  10                  15

Ser Gln Gln Gly Thr Ala Ala Leu Gln Lys Glu Leu Lys Arg Ile Lys
             20                  25                  30

Ile Pro Asp Tyr Ser Asp Ser Phe Lys Ile Lys His Leu Gly Lys Gly
         35                  40                  45

His Tyr Ser Phe Tyr Ser Met Asp Ile Arg Glu Phe Gln Leu Pro Ser
 50                  55                  60                  65

Ser Gln Ile Ser Met Val Pro Asn Val Gly Leu Lys Phe Ser Ile Ser
                 70                  75                  80

Asn Ala Asn Ile Lys Ile Ser Gly Lys Trp Lys Ala Gln Lys Arg Phe
             85                  90                  95

Leu Lys Met Ser Gly Asn Phe Asp Leu Ser Ile Glu Gly Met Ser Ile
        100                 105                 110

Ser Ala Asp Leu Lys Leu Gly Ser Asn Pro Thr Ser Gly Lys Pro Thr
    115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
                150                 155                 160

Ile Glu Ser Ala Leu Arg Asn Lys Met Asn Ser Gln Val Cys Glu Lys
            165                 170                 175

Val Thr Asn Ser Val Ser Ser Lys Leu Gln Pro Tyr Phe Gln Thr Leu
        180                 185                 190

Pro Val Met Thr Lys Ile Asp Ser Val Ala Gly Ile Asn Tyr Gly Leu
    195                 200                 205

Val Ala Pro Pro Ala Thr Thr Ala Glu Thr Leu Asp Val Gln Met Lys
210                 215                 220                 225

Gly Glu Phe Tyr Ser Glu Asn His His Asn Pro Pro Phe Ala Pro
                230                 235                 240

Pro Val Met Glu Phe Pro Ala Ala His Asp Arg Met Val Tyr Leu Gly
            245                 250                 255

Leu Ser Asp Tyr Phe Phe Asn Thr Ala Gly Leu Val Tyr Gln Glu Ala
        260                 265                 270

Gly Val Leu Lys Met Thr Leu Arg Asp Asp Met Ile Pro Lys Glu Ser
    275                 280                 285

Lys Phe Arg Leu Thr Thr Lys Phe Gly Thr Phe Leu Pro Glu Val
290                 295                 300                 305

Ala Lys Lys Phe Pro Asn Met Lys Ile Gln Ile His Val Ser Ala Ser
                310                 315                 320
```

-continued

```
Thr Pro Pro His Leu Ser Val Gln Pro Thr Gly Leu Thr Phe Tyr Pro
            325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
        355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
            405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
        435                 440                 445

Gly Ala Asp Val Val Tyr Lys
450                 455
```